(12) United States Patent
Barton et al.

(10) Patent No.: US 10,144,693 B2
(45) Date of Patent: Dec. 4, 2018

(54) CATALYST FOR THE GAS PHASE PRODUCTION OF CARBOXYLIC ACIDS

(71) Applicant: Dow Global Technologies LLC, Midland, MI (US)

(72) Inventors: David G. Barton, Midland, MI (US); Gerolamo Budroni, Terneuzen (NL); Steven L. F. Corthals, Wachtebeke (BE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/518,060

(22) PCT Filed: Oct. 6, 2015

(86) PCT No.: PCT/US2015/054235
§ 371 (c)(1),
(2) Date: Apr. 10, 2017

(87) PCT Pub. No.: WO2016/060891
PCT Pub. Date: Apr. 21, 2016

(65) Prior Publication Data
US 2017/0313642 A1 Nov. 2, 2017

Related U.S. Application Data

(60) Provisional application No. 62/065,167, filed on Oct. 17, 2014.

(51) Int. Cl.
| | | |
|---|---|---|
| *C07C 51/14* | (2006.01) | |
| *B01J 8/02* | (2006.01) | |
| *B01J 23/74* | (2006.01) | |
| *C01G 51/00* | (2006.01) | |
| *C01G 53/11* | (2006.01) | |
| *C01G 55/00* | (2006.01) | |
| *C07C 53/122* | (2006.01) | |

(52) U.S. Cl.
CPC .......... *C07C 51/14* (2013.01); *B01J 8/0292* (2013.01); *B01J 23/74* (2013.01); *C01G 51/30* (2013.01); *C01G 53/11* (2013.01); *C01G 55/00* (2013.01); *C07C 53/122* (2013.01)

(58) Field of Classification Search
CPC ....... C07C 51/14; C07C 53/122; C07C 11/04; C07C 51/15; C07C 51/50; B01J 23/74; B01J 8/0292; B01J 2219/00033; B01J 2219/00162; B01J 2219/00594; B01J 27/043; C01G 51/30; C01G 53/11; C01G 55/00

See application file for complete search history.

(56) References Cited

U.S. PATENT DOCUMENTS

| | | | |
|---|---|---|---|
| 1,924,767 A | 8/1933 | Carpenter | |
| 2,008,348 A | 7/1935 | Carpenter | |
| 2,089,903 A | 8/1937 | Larson | |
| 2,593,440 A * | 4/1952 | Hagemeyer, Jr. | ........ B01J 27/06 560/232 |
| 3,501,518 A * | 3/1970 | Bittler | ..................... C07C 51/14 554/129 |
| 3,816,490 A | 6/1974 | Forster et al. | |
| 5,866,716 A | 2/1999 | Schafer et al. | |
| 2002/0019562 A1 | 2/2002 | Baird et al. | |

FOREIGN PATENT DOCUMENTS

| | | |
|---|---|---|
| DE | 19725588 A1 | 12/1998 |
| EP | 0495547 A2 | 7/1992 |
| NL | 6516513 A | 6/1966 |
| WO | 0110807 A1 | 2/2001 |

OTHER PUBLICATIONS

Samel, et al: Propionic Acid and Dirivatives, Ullmann's Encyclopedia of Industrial Chemistry, pp. 1-20, 2014.

Cody, et al; Assaying the Catalytic Potential of Transition Metal Sulfides for Abiotic Carbon Fixation, Geochimica Et Cosmochimica Acta, vol. 68, Issue 10, pp. 2185-2196, 2004.

Cody et al; Geochemical Roots of Autotrophic Carbon Fixation: Hydrothermal Experiments in the System Citric Acid, H2O-(+FeS)-(+NiS), Geochimica Et Cosmochimica Acta, vol. 65, Issue 20, pp. 3557-3576, 2001.

Ullmann's Encyclopedia of Industrial Chemistry, 2015, vol. 30, pp. 295-311.

PCT/US2015/054235, International Search Report and Written Opinion dated Dec. 16, 2015.

PCT/US2015/054235, International Preliminary Report on Patentability dated Apr. 27, 2017.

\* cited by examiner

*Primary Examiner* — Jafar F Parsa
*Assistant Examiner* — Blaine G Doletski

(57) ABSTRACT

Carboxylic acids are prepared by a one-step gas phase process comprising the step of contacting under halogen-free hydroxycarbonylation conditions an alkene, carbon monoxide, water, and a solid sulfide-containing catalyst.

12 Claims, No Drawings

CATALYST FOR THE GAS PHASE PRODUCTION OF CARBOXYLIC ACIDS

FIELD OF THE INVENTION

This invention relates to the gas phase production of a carboxylic acid. In one aspect the invention is the gas phase production of a carboxylic acid by the hydroxycarbonylation of an alkene in the presence of water using a heterogeneous sulfide-based metal catalyst.

BACKGROUND OF THE INVENTION

Carboxylic acids, such as propionic acid, are important intermediates for the synthesis of a number of oxygenates that find applications in herbicides, food preservatives, plastics, plasticizers, and cosmetics.

Various methods are known for the production of carboxylic acids. Taking as an example propionic acid, one commercial method relies on the liquid phase hydrocarboxylation of ethylene. Although there are a number of companies that have claimed such a process, including Shell (EP 0 495 547) and Monsanto (U.S. Pat. No. 3,816,490), BASF (U.S. Pat. No. 5,866,716) is the sole manufacturer that exploits this direct liquid phase route. In this process ethylene, CO and water are converted directly into propionic acid in the presence of a highly toxic $Ni(CO)_4$ catalyst at harsh reaction conditions (250-320° C., 100-300 bar).

A second liquid phase method to produce carboxylic acids uses olefin hydroformylation, followed by oxidation of the aldehyde to produce the carboxylic acid. In this commercially practiced, two reaction step, process to produce propionic acid, propanal is produced in the first step via the hydroformylation of ethylene, and in a second step propanal is oxidized to propionic acid ("Ullmann's Encyclopedia of Industrial Chemistry" Vol. 30, pp. 295-311 (2012)).

Another route to produce carboxylic acids is the direct oxidation of hydrocarbons ("Ullmann's Encyclopedia of Industrial Chemistry" Vol. 30, pp. 295-311 (2012)). Direct oxidation of hydrocarbons can also be used to produce propionic acid as a by-product during acetic acid synthesis from naphtha ("Ullmann's Encyclopedia of Industrial Chemistry" Vol. 30, pp. 295-311 (2012)).

The liquid phase single-step hydrocarboxylation of ethylene has an advantage in ethylene yield compared to the two-step hydroformylation/oxidation route; however, it has found limited industrial use because of the cost and risk associated with operating a high pressure reactor that uses a corrosive and toxic nickel carbonyl catalyst.

The processes listed above refer to reactions in the liquid phase. The open literature on gas phase hydrocarboxylation is limited. Early work described the formation of a carboxylic acid via mixing steam with CO and an olefin. Examples of catalysts are charcoal (U.S. Pat. No. 2,089,903), ZnCl (U.S. Pat. No. 1,924,767) and W oxides (U.S. Pat. No. 2,008,348), and in all cases the catalysts were used in combination with metal halides. Although these works indicate a pressure range between 25 and 900 atm, the examples are performed at 600-700 atm.

U.S. Pat. No. 3,501,518 discloses that the carbonylation reaction can by activated by Pd sulfide. The reaction is performed in the liquid phase at a temperature range of 30-180° C. at a pressure of 5-100 MPa (49-987 atm) and requires the addition of halides or co-catalysts such as acids and an organic phosphine or nitrile.

In view of the deficiencies of the prior art methods, it would be desirable to have an alternative catalyst system and process for the gas phase, single step hydrocarboxylation of olefins to carboxylic acids.

SUMMARY OF THE INVENTION

The process of the invention is such a gas phase process comprising producing a carboxylic acid by contacting at a temperature of from more than 250° C. to 400° C. under halogen-free hydroxycarbonylation conditions an alkene, carbon monoxide gas, water and a solid metal sulfide catalyst.

Surprisingly, the reaction proceeds with a metal sulfide catalyst with no need of a halide, or other, co-catalyst, and can proceed at moderate pressures.

DETAILED DESCRIPTION OF THE PREFERRED EMBODIMENT

Definitions

All references to the Periodic Table of the Elements refer to the Periodic Table of the Elements published at page 1-10 of the CRC Handbook of Chemistry and Physics, 71$^{st}$ Ed. (1990-1991). Also, any references to a Group or Groups shall be to the Group or Groups reflected in this Periodic Table of the Elements using the IUPAC system for numbering groups. Unless stated to the contrary, implicit from the context, or customary in the art, all parts and percentages are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, weight percentages, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts of the various reactants in and the operating conditions of the inventive process.

"Composition" and like terms mean a mixture or blend of two or more components.

"Hydroxycarbonylation conditions" and like terms mean the temperature, pressure and other conditions necessary for an alkene, carbon monoxide and water, one or more of which is at least partially in the form of a gas, to react with one another over and in contact with a solid sulfide containing catalyst to form a carboxylic acid. In one embodiment, each of the alkene, CO and water are at least partially in the form of a gas. In one embodiment each of the alkene, CO and water are completely or nearly completely in the form of a gas.

"Halogen-free hydroxycarbonylation conditions" and like terms mean hydroxycarbonylation conditions in which halogen in any form is absent or essentially absent from the space in which the alkene, CO and water are contacted over a sulfide containing catalyst to form an carboxylic acid. "Essentially absent" means, in the context of a halogen, that any halogen present in the reaction space is present in an amount that does not materially affect the conversion or selectivity of the reactants to the desired carboxylic acid. The source of such halogen can be, for example, from one or more of the feeds to the reaction or the catalyst (as, for example, a contaminant), or from the surface of a piece of equipment, etc. In one embodiment "halogen-free" means less than 1000 parts per million (ppm), preferably less than 10 ppm, and more preferably less than 1 ppm, based on the combined weight of the reactants.

Production of the Carboxylic Acid

Reactants

In one embodiment, the invention is a process for the production of a carboxylic acid from an alkene, carbon monoxide and water. The alkene can be either mono-, or polyolefinic, i.e., containing more than one double bond. The mono-olefinic alkene is of the formula $C_nH_{2n}$ in which n is an integer greater than 1, typically 2-12 and more typically 2-8. Most typically and preferably n is 2, i.e., the alkene is ethylene. Mixtures of alkenes may be employed. For example, commercial alpha olefins containing four or more carbon atoms may contain minor amounts of corresponding internal olefins and/or their corresponding saturated hydrocarbon and that such commercial alkenes need not necessarily be purified from same prior to use.

The carbon monoxide can be used neat or in combination with one or more other gases that are inert with the reaction reagents, products and by-products under reaction conditions. These other gases include, but are not limited to, nitrogen, carbon dioxide and the noble gases.

The terms "alkene" and "olefin" are used interchangeably herein. Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexene, 2-heptene, 2-octene, cyclohexene, butadiene, styrene, 1,4-hexadiene, 1,7-octadiene, as well as alkyl alkenoates, alkenyl alkanoates, alkenyl alkyl ethers, alkenols, alkenals, and the like. Like the carbon monoxide, the alkene may comprise other compounds, such as impurities and contaminants. In the case of the alkene, some of these compounds may be present as a result of the process in which the alkene was formed. For example, a methane-containing source, such as shale gas or natural gas, can be converted to an alkene via techniques well-known to those skilled in the art. Depending on the alkene production process, by-products such as CO, $H_2$, $CO_2$ and/or others can be present in the alkene. Thus, in one embodiment the invention is a gas phase process comprising producing a carboxylic acid by contacting at a temperature of from more than 250° C. to 400° C. under halogen-free hydroxycarbonylation conditions an alkene, carbon monoxide gas, water and a solid metal sulfide catalyst, with the proviso that the alkene, preferably ethylene, is derived from a methane-containing source, such as shale gas or natural gas.

Water (liquid or gaseous) can be pure or diluted. In one embodiment of the invention, the water can be provided at least partially by any precursor that provides water, including alcohols, acids and other oxygenates.

Catalyst

The catalyst is a sulfide containing catalyst, particularly a metal sulfide catalyst, and can be in bulk or in supported form. The catalyst can comprise one or more metals. Typically the catalyst comprises at least one Group VIII metal, e.g., iron, cobalt, nickel, rhodium, etc., and it can contain one or more other metals as well, e.g., a Group IA metal such as potassium or another transition metal such as titanium, vanadium, chromium, manganese, copper, zinc, tungsten and the like. In one embodiment of the invention, the catalyst comprises at least one Group VIII metal other than Pd. In one embodiment of the invention, the catalyst comprises at least one of iron, cobalt, nickel, rhodium and, ruthenium. In one embodiment of the invention, the catalyst comprises at least one of iron, cobalt, nickel, and, ruthenium. The catalyst is a sulfide, which means that at least one metal of the catalyst is bonded covalently or ionicly to at least one sulfur atom. Examples of catalysts for use in this invention include, but are not limited to, iron sulfide, cobalt sulfide, ruthenium sulfide, potassium rhodium sulfide and nickel sulfide.

The preparation of metal sulfides is well known in the art, and they can be prepared by various processes, such as precipitation/coprecipitation. For example cobalt sulfide can be prepared by precipitation of an aqueous solution of $(NH_4)_2S$ and an aqueous cobalt salt solution, such as a cobalt nitrate solution. The precipitate is filtered, dried and treated in a furnace at, for example 500° C., under a nitrogen gas blanket. Purchased cobalt sulfides are also effective catalysts such as, for example, CAS 1317-42-6 available from suppliers such as Sigma Aldrich and Materion.

The catalyst can be supported. Examples of supports include alumina, alpha alumina, gamma alumina, silica, silica-alumina, zeolite, magnesia, magnesium hydroxide, titania, calcium carbonate, activated carbon, and the like. The preparation of supported catalysts is well known in the art.

Process Conditions and Equipment

The process of this invention is conducted in the gas phase over a solid catalyst. As such, in one embodiment of the invention, the alkene, CO and water are introduced as gases and contacted with one another over and in contact with a solid catalyst bed. The reactants can be introduced in a single or multiple feed streams. The molar ratio of CO to alkene is typically at least 1:1, typically at least 3:1, more typically from 3:1 to 50:1 and even more typically from 3:1 to 15:1. The molar ratio of alkene to water is typically at least 0.1:1, more typically at least 0.5:1, more typically from 0.1:1 to 10:1 and even more typically from 0.2:1 to 2:1.

Although the process can be operated in either a continuous or batch mode, the process is preferably operated in a continuous mode.

The process temperature can be from over 250° C. to 450° C., from 260° C. to 400° C., or from 280° C. to 350° C. The total pressure of the process can be from 0.1 to 30 MPa, or from 1.5 to 6 MPa. The gas hourly space velocity of the process is typically from 100 to 1,000,000 liters of gas feed per liter of catalyst per hour (L/L*h), more typically from 500 to 5,000 L/L*hr.

In one embodiment, the reaction is conducted in a fixed-bed reactor. In one embodiment the reactor is a tube reactor. In a typical protocol, the temperature and pressure are slowly increased to the reaction conditions. The catalyst can be exposed to a feed comprising an inert gas (such as nitrogen or helium), carbon monoxide, alkenes, water, optionally a small amount of a sulfur-containing gas, such as $H_2S$, and any combination of the above. Examples of other sulfur-containing gases include but are not limited to mercaptans, thiophenes, dimethyl sulfide and dimethyl disulfide. The feed gas may also include impurities or contaminants such as, for example, hydrogen. The effluent gas from the reactor can be analyzed via gas chromatography (GC) to determine the product composition and the amount of CO converted.

In one embodiment, the reactor is a trickle bed reactor in which the catalyst is a solid and at least one of the reactants is at least partially in the gas phase. Typically, the alkene and carbon monoxide are completely gaseous but the water, and in some embodiments the alkene, depending upon its boiling point and the hydroxycarbonylation conditions, may be partially or totally liquid. For purposes of this invention, a process, such as that conducted in a trickle-bed reactor, is considered a gas phase process as long as at least one of the alkene, CO and water is at least partially, preferably mostly, and more preferably completely or nearly completely, in the gas phase. Typically in such a process, the alkene and CO are completely or nearly completely in the gaseous phase under hydroxycarbonylation conditions.

EXAMPLES

Catalyst Synthesis:

Synthesis using metal nitrate precursor. Cobalt sulfide is prepared by precipitation of an aqueous solution of $Co(NO_3)_2 \cdot H_2O$ (9.6 g $Co(NO_3)_2$ (purchased from Aldrich) in 19.2 ml $H_2O$) with an aqueous solution of $(NH_4)_2S$ (20%) (purchased from Aldrich) in 40 ml of $H_2O$ in an oil bath at 60° C. After precipitation, the samples are left at 60° C. for about 15 minutes and are then cooled to room temperature. The precipitate is filtered using a vacuum pump and "Whatman 3" qualitative filter paper, is dried and is thermally treated at 500° C. under a 200 ml/min $N_2$ flow for 1 hr in a furnace.

Synthesis using metal chloride precursor: Metal (Ni, Ru and Fe) sulfide catalysts are prepared according to the following precipitation method with $(NH_4)_2S$ and the corresponding metal chloride hydrates. 3.3 M solutions of metal chloride salts and an aqueous $(NH_4)_2S$ solution (20 wt %) are added dropwise within 10 minutes to 40 ml $H_2O$ in a beaker, which then is placed in a 60° C. oil bath. After precipitation, samples are left at 60° C. for about 15 minutes and then cooled to room temperature. The precipitate is filtered using a Büchner funnel, vacuum pump and "Whatman 3" qualitative filter paper, and the powder is washed with 600 ml of $H_2O$. Samples are dried at 50° C. for 20 h. Finally, samples are thermally treated at the same conditions as the cobalt sulfide.

Example 1

The gas phase hydroxycarbonylation of ethylene with CO and water is conducted in a fixed-bed, high pressure microreactor. The nickel sulfide catalyst prepared hereinabove (250 microliters) is tested at 5 MPa under a flow of carbon monoxide, water and ethylene (nitrogen is added as an internal standard) at 290° C. The composition of the feed and the conditions tested are reported in Table 1, except that the gas hourly space velocity is shown in Table 2. The results are shown in Table 2. Selectivities are based on mole % carbon.

Example 2

The reaction conditions are the same as in Example 1 except that iron sulfide prepared hereinabove is employed as the catalyst. The results are shown in Table 2.

Example 3

The reaction conditions are the same as in Example 1 except that ruthenium sulfide prepared hereinabove is employed as the catalyst. The results are shown in Table 2.

Example 4

The reaction conditions are the same as in Example 1 except that cobalt sulfide is employed as the catalyst (250-500 microliters) under 2 different gas hourly space velocities (GHSV). The results are shown in Table 2, and designated Ex. 4A and 4B.

Example 5

The reaction conditions are the same as in Example 1 except that $CoS_2$ purchased from Materion, specifically $CoS_2$ available at http://www.materion.com/Businesses/AdvancedMateriaisGroup/About/InorganicChemicalsCatalog.aspx, is employed as the catalyst (500 microliters). The results are shown in Table 2.

TABLE 1

| Reaction Conditions | | | | | |
|---|---|---|---|---|---|
| CO (Vol %) | $H_2O$ (Vol %) | $C_2H_4$ (Vol %) | $N_2$ (Vol %) | P (barg) | Temp (° C.) |
| 70 | 10 | 10 | 10 | 50 | 290 | barg = bars, gauge

TABLE 2

| Catalyst performance for propionic acid (PA) synthesis. | | | | | | | | |
|---|---|---|---|---|---|---|---|---|
| Example | Catalyst | Conv %_Carbon | GHSV (1/h) | Sel %_PA | Sel %_HC | Sel %_$CO_2$ | Sel %_MeP | Sel %_AcH |
| 1 | NiS$x$ | 2.0 | 3023 | 87.9 | 1.6 | 4.1 | 5.1 | 0.6 |
| 2 | FeS$x$ | 0.7 | 3118 | 38.5 | 30.3 | 27.5 | 3.7 | 0.0 |
| 3 | RuS$x$ | 0.3 | 3440 | 84.0 | 2.0 | 10.0 | 0.0 | 4.0 |
| 4A | CoS$x$ | 15.9 | 2876 | 88.1 | 4.1 | 6.4 | 0.0 | 0.1 |

TABLE 2-continued

Catalyst performance for propionic acid (PA) synthesis.

| Example | Catalyst | Conv %_Carbon | GHSV (1/h) | Sel %_PA | Sel %_HC | Sel %_$CO_2$ | Sel %_MeP | Sel %_AcH |
|---|---|---|---|---|---|---|---|---|
| 4B | CoS$x$ | 18.0 | 1410 | 85.2 | 5.7 | 7.7 | 0.0 | 0.2 |
| 5 | CoS2 | 12.5 | 1545 | 91.5 | 1.9 | 5.7 | 0.0 | 0.2 |

Sel % = selectivity based on mole % carbon.
Sel %_HC = sum selectivities of $C_1$ to $C_6$ alkanes and alkenes.
MeP: methyl propionate,
ACH: acetaldehyde,
PA: propionic acid

What is claimed is:

1. A gas phase process comprising producing a carboxylic acid by contacting at a temperature of from more than 250° C. to 400° C. under halogen-free hydroxycarbonylation conditions an alkene, carbon monoxide gas, water and a solid metal sulfide catalyst comprising at least one Group VIII metal, other than Pd.

2. The process of claim 1 in which the catalyst comprises at least one of cobalt, nickel, rhodium and, ruthenium.

3. The process of claim 2 in which the catalyst comprises at least one of cobalt, nickel, and, ruthenium.

4. The process of claim 1 in which the alkene comprises at least one alkene selected from the group of (a) a monoolefinic alkene and (b) a polyolefinic alkene.

5. The process of claim 1 wherein the process is continuous.

6. The process of claim 1 in which the alkene is ethylene in the gas phase.

7. The process of claim 1 in which the hydroxycarbonylation conditions include a pressure from 0.1 MPa to 10 MPa.

8. The process of claim 1 conducted in a trickle-bed reactor.

9. The process of claim 1 wherein the catalyst is supported.

10. The process of claim 1 wherein the catalyst is cobalt sulfide.

11. The process of claim 1 wherein the alkene is ethylene.

12. A gas phase, continuous process comprising producing propionic acid by contacting at a temperature of from more than 250° C. to 400° C., at a pressure of 0.1 MPa to 10 MPa, and under hydroxycarbonylation conditions ethylene, carbon monoxide gas, water and a solid metal sulfide catalyst comprising at least one Group VIII metal, other than Pd, wherein the process comprises less than 1 ppm halogen based on the combined weight of the reactants.

* * * * *